United States Patent [19]

Yamamoto et al.

[11] Patent Number: 4,611,055
[45] Date of Patent: Sep. 9, 1986

[54] PRODUCTION OF SUCROSE FATTY ACID POLYESTER

[75] Inventors: Toshiaki Yamamoto, Ohtsu; Kenichi Kinami, Kyoto, both of Japan

[73] Assignee: Dai-Ichi Kogyo Seiyaku Co., Ltd., Kyoto, Japan

[21] Appl. No.: 748,793

[22] Filed: Jun. 26, 1985

[30] Foreign Application Priority Data

Jun. 29, 1984 [JP] Japan .................................. 59-136383

[51] Int. Cl.$^4$ ............................................ C07H 13/06
[52] U.S. Cl. .................... 536/119; 536/115; 536/127
[58] Field of Search ........................ 536/119, 115, 127

[56] References Cited

U.S. PATENT DOCUMENTS

| | | | |
|---|---|---|---|
| 3,251,827 | 5/1966 | Schnell et al. | 536/119 |
| 3,963,699 | 6/1976 | Rizzi et al. | 536/119 |
| 3,996,206 | 12/1976 | Parker et al. | 536/119 |
| 4,032,702 | 6/1977 | James | 536/119 |
| 4,298,730 | 11/1981 | Galleymore et al. | 536/119 |
| 4,377,685 | 3/1983 | Bouniot et al. | 536/119 |
| 4,517,360 | 5/1985 | Volpenhein | 536/119 |
| 4,518,772 | 5/1985 | Volpenhein | 536/119 |

*Primary Examiner*—Johnnie R. Brown
*Attorney, Agent, or Firm*—Millen & White

[57] ABSTRACT

Sucrose fatty acid polyesters are produced by heating a molten mixture of sucrose, fatty acid lower alkyl ester, transesterification catalyst, fatty acid alkali metal soap and/or sucrose fatty acid ester. Sucrose fatty acid polyesters are purified by acidifying the reaction product and subjecting the acidified reaction product to molecular distillation whereby the sucrose fatty acid polyesters are recovered as the residue.

19 Claims, No Drawings

PRODUCTION OF SUCROSE FATTY ACID POLYESTER

BACKGROUND OF THE INVENTION

Sucrose fatty acid esters are conventionally prepared by transesterifying a lower alkyl ester of higher fatty acid with sucrose. Since sucrose has eight hydroxyl groups per molecule, the number of fatty acid groups bound to sucrose per molecule (commonly referred to as "degree of substitution" or "D.S.") may vary from 1 to 8. Among them, mono-, di- and tri-esters find use as non-toxic, biodegradable surfactants and are commercially available in large quantities.

Sucrose fatty acid polyesters having a D.S. of at least 4, preferably at least 6 have been reported to be effective in the treatment of hypercholesteremia. See, Chemical & Engineering News, p.26, Dec. 4, 1978; U.S. Pat. No. 4,005,195; U.S. Pat. No. 4,005,196; European Patent Application No. 69,412 (Jan. 12, 1983); and German Patent Publication No. 2,648,551.

The present invention is directed to the production of such sucrose fatty acid polyesters.

Various methods are known for producing sucrose-fatty acid esters. They may be classified into the following three principal types.

In the solvent process, a fatty acid ester is transesterified with sucrose in a common solvent for the fatty acid ester and sucrose such as dimethylformamide or dimethylsulfoxide in the presence of a basic transesterification catalyst. The reaction may be carried out even at a relatively lower temperature, for example, at about 90° C. This process suffers from certain disadvantages that the solvent used is toxic and, therefore, must be completely removed after the reaction. This is possible in practice only with great difficulty.

In the second process generally known as "microemulsion process", a fatty acid ester is dispersed in a solution of sucrose in a solvent such as propylene glycol or water with the aid of an emulsifier such as alkali metal fatty acid soaps to form a microemulsion, and then the solvent is removed from the emulsion. The reaction is carried out in the absence of solvent and the reaction product does not contain any solvent. Great difficulty is also present in this process for removing the solvent while maintaining the microemulsion state.

In the third process, sucrose is directly reacted with a fatty acid ester by heating their mixture. This process is known as "direct process" or "solvent-free process". Since sucrose and fatty acid esters do not have sufficient affinity to each other, the success of this direct process depends on how they are well contacted in the reaction system. To this end, most of known processes employ an alkali metal fatty acid soap either directly added to or formed in situ in the reaction system to produce a homogeneous molten mixture of reactants.

Consequently, the reaction mixture from the microemulsion process or direct process contains a relatively large amount of alkali metal fatty acid soap, since the soap itself is not a reactant and remains unreacted during the transesterification reaction.

A relatively small amount of alkali metal fatty acid soap is unavoidably formed even in the solvent process by the reaction between the fatty acid ester and the transesterification catalyst such as alkali metal hydroxides and carbonates.

Normally, alkali metal fatty acid soaps remaining in the reaction mixture are separated from sucrose fatty acid esters, while their presence may be tolerated in certain uses such as detergents.

Sucrose fatty acid polyesters may be advantageously produced by the microemulsion process or solvent-free process.

U.S. Pat. No. 3,963,699 to Rizzi et al. discloses a process for producing sucrose fatty acid polyesters. According to this process, a mixture of sucrose, a fatty acid lower alkyl ester, an alkali metal fatty acid soap and a basic catalyst is heated in the first step to form a homogeneous melt. Thereafter, excess fatty acid lower alkyl esters are added in the second step to the reaction product of the first step. This process suffers from certain disadvantages in that it requires such basic transesterification catalysts as alkali metals, alloys of alkali metals, alkali metal hydrides or alkali metal alkoxides which are expensive and dangerous in handling. The two step reaction is cumbersome in operation and necessarily requires a prolonged reaction time which can lead to the risk of darkening of the reaction mixture.

Generally, sucrose fatty acid esters having a D.S. of greater than 2 are produced by controlling the molar ratio of fatty acid lower alkyl esters to sucrose. Up to a D.S. of 5, polyesters may be prepared at the ratio of fatty acid esters approximately equal to or slightly excess of theoretical amounts. However, polyesters having a D.S. of greater than 5 require further excess of fatty acid lower alkyl esters. For example polyesters having D.S. of 5.5, 6 and 7 or higher may only be produced at the ratio of fatty acid esters of about 6, 8 and 10 moles per mole of sucrose, respectively. Thus, it is critical for the industrial production of sucrose fatty acid polyesters to minimize the amount of fatty acid lower alkyl esters.

The presence of large amounts of fatty acid lower alkyl esters in the reaction system at one time produces certain unique problems. A reaction system containing a large amount of fatty acid esters is less viscous and thus easily susceptible to phase separation which adversely affects the transesterification reaction. Furthermore, relatively large amounts of low boiling-point by-products such as methanol are generated and vigorous foaming of reactants takes place during the initial period of the reaction.

It is therefore an object of the present invention to provide a process for producing sucrose fatty acid polyesters in an efficient manner which is free from the above-described disadvantages and which is simple in operation and easy to control.

As previously noted, sucrose fatty acid esters in the reaction product must be separated from impurities mainly consisting of unreacted fatty acid lower alkyl esters and fatty acid alkali metal soaps.

Fatty acid lower alkyl esters may be removed from the reaction product by solvent extraction using a solvent such as methanol in which sucrose fatty acid esters are relatively insoluble and fatty acid lower alkyl esters are soluble. However, this technique requires a large amount of solvent. For example, about 40 times of methanol are used relative to the sucrose fatty acid ester in the previously cited Rizzi et al. patent. This is of course uneconomical and requires a large amount of investment to solvent recovery system and anti-explosion facilities. Additionally, certain amounts of sucrose fatty acid esters dissolving in the solvent are unavoidably wasted.

Japanese Patent Publication No. 28890/1973 discloses a method for selectively extracting sucrose fatty acid esters from the reaction product containing fatty acid alkali metal soaps with acetone. Unfortunately, this method is applicable only to sucrose fatty acid lower esters but not effective to sucrose fatty acid polyesters because the polyesters are not sufficiently soluble in acetone.

Japanese Patent Publication No. 37168/1975 discloses a method for separating fatty acid alkali metal soap from the reaction product containing sucrose fatty acid esters. The method comprises the steps of dissolving or suspending the reaction product in water or a mixture of water and an organic solvent, adding thereto a water-soluble salt of a multivalent metal to form a water-insoluble metallic soap and separating the metallic soap. This method is also inapplicable to sucrose fatty acid polyesters because appreciable amounts of metallic soap are soluble in the sucrose polyesters.

We have found that fatty acid alkali metal soaps may be removed by leaching the reaction product with an aqueous mixture containing about 20% of a lower alkanol which effectively prevents emulsifying of the entire system. Again, the use of organic solvents is uneconomical and must suffer from various disadvantages as previously discussed.

None of known processes permits separation of both fatty acid lower alkyl esters and alkali metal soaps from sucrose fatty acid polyesters simultaneously.

It is therefore a further object of the present invention to provide a process for isolating sucrose fatty acid polyesters from the reaction product containing the polyester, fatty acid lower alkyl esters and alkali metal soaps in an economical and simple manner.

Other objects and advantages of the present invention will become apparent as the description proceeds.

SUMMARY OF THE INVENTION

It has now been found that sucrose fatty acid polyesters may be produced in a high yield within a relatively short reaction time by heating a molten mixture of sucrose, at least 4 moles per mole of sucrose of a fatty acid lower alkyl ester, a basic transesterification catalyst, a fatty acid alkali metal soap and/or a sucrose fatty acid ester at a temperature from 120° C. to 180° C. under a vacuum less than 10 mmHg with stirring at a linear speed of 1.0 to 50 m/second.

According to the present invention the resulting reaction product may be purified by subjecting the crude reaction product to molecular distillation to remove unreacted fatty acid lower alkyl ester. Preferably, the crude reaction product is acidified to a pH below 6 prior to the molecular distillation to decompose fatty acid alkali metal soap to corresponding free fatty acid. The formed free fatty acid may be removed together with fatty acid lower alkyl ester by the molecular distillation.

DETAILED DESCRIPTION OF THE INVENTION

The term "sucrose fatty acid polyesters" as used herein refers to as those having an average degree of substitution of 4 to 8.

Any commercially available solid sucrose of any grade and size such as granulated sugar or refined white sugar may be used in the process of the present invention.

The term "fatty acid lower alkyl esters" as used herein is intended to include the $C_1$ to $C_4$ alkyl esters of fatty acids containing 6 to 22 carbon atoms. The fatty acids may be saturated or unsaturated and may have a straight or branched chain. Mixtures of fatty acid esters may also be used. From 4 to 15 moles, preferably from 8 to 15 moles per mole of sucrose of fatty acid lower alkyl esters are used.

Examples of basic transesterification catalysts include alkali metal carbonates such as potassium carbonate and sodium carbonate, alkali metal hydroxides such as potassium hydroxide and sodium hydroxide, alkali metal lower alkoxide such as potassium methoxide and sodium ethoxide. Carbonates and hydroxides of sodium and potassium are preferable to give higher yields of sucrose fatty acid polyesters. The catalyst is added to the reaction mixture in an amount of 1 to 10%, preferably 3 to 8% by weight of fatty acid lower alkyl esters.

The term "fatty acid alkali metal soap" as used herein refers to the alkali metal salts of $C_6$–$C_{22}$ fatty acids. Sodium, potassium and lithium salts may be used. From 3 to 15%, preferably 5 to 10% of the soap is used relative to the total weights of sucrose and fatty acid lower alkyl esters.

The fatty acid alkali metal soap may be replaced entirely or partially with a sucrose fatty acid ester. A variety of sucrose fatty acid esters having an average D.S. of 1 to 8 may be used. When sucrose fatty acid esters alone are used, from 3 to 30%, preferably 5 to 15% relative to the total weights of sucrose and fatty acid lower alkyl esters is suitable. The sucrose fatty acid ester used for this purpose may be recovered and reused in the next run without purification when the fatty acid alkali metal soap is not added externally.

Fatty acid alkali metal soap and/or sucrose fatty acid ester may be added to sucrose and fatty acid lower alkyl esters in any desired manner prior to the transesterification reaction. Preferably, the soap and/or sucrose ester are molten at a temperature above 70° C., preferably from 90° C. to 110° C.

Other reactants, e.g. sucrose, fatty acid lower alkyl esters and catalyst are added to the melt.

The transesterification may be carried out by heating the reaction mixture at a temperature of 120° C. to 180° C., preferably from 140° C. to 160° C. under a vacuum less than 10 mmHg with stirring at a linear speed of 1.0 to 50 m/second, preferably from 2.0 to 20 m/second.

The term "linear speed" as used herein may be represend by the formula: $R°2\pi L$, wherein R is the revolutions per second of stirring means employed, and L is the length of stirring blade measured from its axis of rotation to the distal end thereof. Within this range of linear speed, phase separation and excessive foaming of the reaction mixture may be effectively prevented.

Examples of useable stirring devices include propeller mixers, turbine screw mixers, dispersers, homogenizers and similar devices. Baffle means may be provided within the reactor to enhance the stirring effect.

The length of reaction time varies with the reaction conditions and generally requires only for 1 to 3 hours.

The resulting reaction product contains, in addition to the desired sucrose fatty acid polyesters, unreacted fatty acid lower alkyl esters, fatty acid alkali metal soap and/or sucrose fatty acid ester.

According to the present invention, the reaction product is acidified to a pH below 6 by an acid to decompose the fatty acid alkali metal soap to corresponding free fatty acid and then subjected to molecular distillation to remove the free fatty acid and unreacted fatty acid lower alkyl esters simultaneously.

Examples of acids which may be used to decompose the fatty acid alkali metal soap include hydrochloric acid, sulfuric acid, phosphoric acid, formic acid, acetic acid, lactic acid, malic acid, succinic acid, sodium hydrogen sulfate, sodium dihydrogen phosphate and the like. An amount of acid at least equal to or slightly excess of the equivalent to the amount of fatty acid alkali metal soap present in the reaction product should be added. This may be performed by simply acidifying the reaction product to a pH below 6, preferably below 5.

The acidified mixture is then subjected to molecular distillation to remove the resulting free fatty acid and unreacted fatty acid lower alkyl ester simultaneously. The desired sucrose fatty acid polyesters may be obtained as the residue. The end product may be further purified as desired by washing with water to remove water-soluble inorganic contaminants and coloring matters.

There are three types of molecular distillers, namely pot type, falling film type and centrifugal type. Molecular distillers of the centrifugal type are preferable.

The molecular distillation according to the present invention may be performed under a vacuum of less than 1 mmHg, preferably from $10^{-1}$ to $10^{-3}$ mmHg at a temperature from 60° to 150° C., preferably from 80° C. to 120° C. Another critical factor is the film thickness. A thickness of less than 1 mm, preferably from $10^{-1}$ to to $10^{-2}$ mm may be employed. To this end, centrifugal molecular distillers are used to advantages, while falling film molecular distillers using a film thickness greater than 1 mm and pot molecular distillers are not suitable for the purposes of the present invention.

As is well-known in the art, molecular distillation is characterized by the use of a very thin film of raw materials for distillation under high vacuum. This technique is mainly utilized to purify heat-degradable substances such as vitamins by distillation at relatively lower temperatures.

Long-chain fatty acids and their lower alkyl esters have boiling points above 200° C. or higher at the atmospheric pressure. Sucrose fatty acid esters are susceptible to thermal decomposition at a temperature above 170° C.

We have discovered that long-chain fatty acids and their lower alkyl esters may be separated from sucrose fatty acid polyesters by molecular distilling their mixture at a temperature at which the sucrose fatty acid polyesters are stable. Contrary to known applications of molecular distillation, target components are obtained as the residue rather than the distillate by the process of the present invention. The contents of free fatty acids and/or their lower alkyl esters may be decreased to less than 1% without degradation and darkening of the targent polyesters. The recovered fatty acids and their lower alkyl esters are also substantially free from undesired contaminats and may be reused as such. Since no solvent is used for the purification of the end product, the process of this invention is more economical and gives purer end product than the prior art solvent extraction technique.

The following examples will further illustrate the present invention. All percents therein are by weight.

EXAMPLE 1

A one liter flask equipped with a thermometer, evacuating means and a propeller type stirrer (rotational radius of 43 mm) was charged with 35.5 g of sodium stearate soap. The soap was heated at a temperature of 90°–110° C. to a molten state. To this were added 53.9 g (0.158 moles) of sucrose, 563.6 g (1.891 moles) of methyl stearate and 17.5 g of potassium carbonate. The mixture was reacted at 160° C. under a vacuum of 5 mmHg with stirring at a linear speed of 11.2 m/sec. for three hours.

During the reaction, foaming of the mixture was not observed whatsoever. Analysis of the reaction product showed a sucrose stearate content of 66.9%, a methyl stearate content of 21.2% and a stearate soap content of 9.8%. The average D.S. of the sucrose stearate calculated from its hydroxyl value was 7.8. High speed liquid chromatography indicated that the sucrose stearate consisted of 29.8% of heptaester and 70.2% of octaester.

For comparison, the above procedure was repeated except that the reaction was carried out at a linear speed of stirring blades of 0.5 m/sec. Vigorous foaming was observed 10 minutes after the beginning of the reaction. In order to avoid spilling of the reacion mixture out of the flask, the degree of vacuum had to be decreased to 80 mmHg after 20 minutes. Analysis of the reaction product showed a sucrose stearate content of 43.2%. The average D.S. calculated from the hydroxyl value was 5.6.

EXAMPLE 2

A 3 liter flask equipped with a thermometer, evacuating means and a turbine type stirrer (rotational radius of 6 cm) was charged with 221.3 g (0.647 moles) of sucrose, 1501.0 g (5.176 moles) of methyl oleate, 200.0 g of sucrose oleate (D.S. of 1.5) and 77.7 g of sodium carbonate. The mixture was heated at a temperature of 90°–110° C. with stirring to a molten state and then reacted at 150° C. under a vacuum of 3 mmHg with stirring at a linear speed of 3 m/sec. for 1.5 hours.

During the reaction, foaming of the mixture was not observed whatsoever. Analysis of the reaction product showed a sucrose oleate content of 87.4%, a methyl oleate content of 7.4% and a sodium oleate soap content of 5.2%. The average D.S. of sucrose oleate calculated from the hydroxyl value was 6.5. High speed liquid chromatography indicated that the sucrose oleate consisted of 5.6% of pentaester, 34.5% of hexaester, 38.9% of heptaester and 21.0% of octaester.

For comparison, the above procedure was repeated except that the reaction was carried out at a linear speed of 0.8 m/sec. Foaming was observed 30 minutes after the beginning of the reaction but it was possible to continue the reaction for 1.5 hours without decreasing the degree of vacuum. Analysis of the reaction product showed a sucrose oleate content of 56.3%. The average D.S. based on the hydroxyl value was 4.3. These results indicated that the reaction rate decreased with the decrease in linear speed.

EXAMPLE 3

The same flask as used in Example 2 was charged with 150.8 g (0.44 moles) of sucrose, 1914 g (6.60 moles) of methyl oleate and 220 g of potassium oleate soap. The mixture was heated to a molten state with stirring. The temperature was raised to 125° C. while evaporating water under vacuum. 150 g of a 40% aqueous solution of sodium hydroxide was added gradually. Then mixture was reacted at 150° C. under a vacuum of 5 mmHg with stirring at a linear speed of 5.2 m/sec. for 2.5 hours.

The resulting reaction product contained 43.5% of sucrose oleate having an average D.S. of 7.4, 35.3% of unreacted methyl oleate and 18.4% of oleate soap.

EXAMPLE 4

A 200 liter stainless-steel reacter equipped with a turbine type stirres (rotational radius of 15 cm) and thermometer, evacuating means was charged with 15.0kg of sodium oleate soap. The soap was heated at a temperature of 160° C. To this were added 9.0kg (26.32 moles) of sucrose, 115.3kg (397.41 moles) of methyl oleate and 7.0kg of potassium hydroxide. The mixture was reacted at 155° C. under a vacuum of 3 mmHg with stirring at a linear speed of 7.5 m/sec. for three hours.

During the reaction, forming of the mixture was not observed. Analysis of the reaction product showed a sucrose oleate content of 54.8%, a methyl oleate content of 32.7% and a oleate soap content of 12.1%. The average D.S. of the sucrose oleate was 7.5 calculated from it OH value.

For comparison, the above procedure was repeated except that the reaction was carried out at a linear speed 0.8 m/sec. Vigorous forming was observed 15 minutes after the beginning of the reaction and further reaction became impossible under these conditions. Therefore, the reaction was continued under a vacuum of 250 mmHg for 5 hours. Analysis of the reaction product showed a sucrose oleate content 37.4%. The average D.S. calculated from the OH value was 5.8.

EXAMPLE 5

200 g of the reaction product prepared in Example 1 was acidified with phosphoric acid at a pH of 4.5 and then subjected to molecular distillation using a centrifugal molecular distillation apparatus at a temperature of 115°-117° C. under a vacuum of $1.5 \times 10^{-1}$ mmHg at a film thickness less than 0.1 mm.

136.4 g of sucrose polystearate was obtained as a pale yellow residue containing 0.2% of soap, 0.7% of stearic acid, 0.4% of methyl stearate and 2.6% of inorganic phosphoric salts. 97.7% of sucrose polystearate was recovered at a purity of 96.1%.

EXAMPLE 6

450 g of the reaction product prepared in Example 2 was acidified with hydrochloric acid at a pH of 3.8 and then subjected molecular distillation using a centrifugal molecular distillation apparatus at a temperature of 107°-108° C. under a vacuum of $6 \times 10^{-2}$ mmHg at a film thickness less than 0.1 mm. The resulting residue was washed with water to remove potassium chloride.

389 g of sucrose polyoleate was obtained as a pale yellow oil containing 0.5% of oleic acid and 0.3% of methyl oleate. 98.3% of sucrose polyoleate was recovered at a purity of 99.2%.

EXAMPLES 7-11 AND COMPARATIVE EXAMPLES 1-4

The reaction product obtained in Example 3 was purified as in Examples 5 and 6. Conditions and results are shown in the following table.

|  | Example | | | | | Comparative Example | | | |
| --- | --- | --- | --- | --- | --- | --- | --- | --- | --- |
|  | 7 | 8 | 9 | 10 | 11 | 1 | 2 | 3 | 4 |
| Reaction product, g | 200 | 200 | 200 | 200 | 200 | 200 | 50 | 200 | 200 |
| Acid treatment |  |  |  |  |  |  |  |  |  |
| Acid | HCl | HCl | Acetic | $H_3PO_4$ | Lactic | None | HCl | HCl | HCl |
| pH | 4.0 | 3.8 | 5.4 | 4.7 | 5.0 | — | 4.0 | 4.1 | 3.9 |
| Molecular Distillation |  |  |  |  |  |  |  |  |  |
| Apparatus Type | A[1] | A | A | B[2] | B | B | C[3] | A | B |
| Vacuum, mmHg | $1.5 \times 10^{-1}$ | $9 \times 10^{-2}$ | $6 \times 10^{-3}$ | $3 \times 10^{-1}$ | $7 \times 10^{-2}$ | $2.5 \times 10^{-2}$ | $4 \times 10^{-2}$ | 2.5 | $6 \times 10^{-2}$ |
| Temperature, °C. | 120-121 | 117-118 | 93-95 | 126-127 | 121-123 | 118-119 | 127-128 | 125-126 | 128-129 |
| Film thickness, mm | <0.1 | <0.1 | <0.1 | 0.2 | 0.5 | 0.2 | 15 | <0.1 | 1.5 |
| Polyester |  |  |  |  |  |  |  |  |  |
| Yield, g | 86.6 | 86.0 | 86.6 | 86.6 | 86.4 | 122.0 | 41.4 | 128.8 | 108.7 |
| Soap, % | 0.1 | 0 | 0.1 | 0.2 | 0.3 | 24.2 | 0.1 | 0.1 | 0.2 |
| Oleic acid, % | 0.9 | 0.7 | 0.7 | 0.5 | 0.8 | 1.2 | 15.5 | 16.2 | 14.3 |
| Methyl oleate, % | 0.5 | 0.4 | 0.3 | 0.2 | 0.5 | 0.3 | 31.8 | 29.9 | 17.1 |
| Inorganic salt, % | 0 | 0.1 | 0.1 | 0 | 0.2 | 4.4 | 4.2 | 0.3 | 0.7 |
| Purity, % | 98.5 | 98.8 | 98.8 | 99.1 | 98.2 | 69.9 | 51.6 | 53.5 | 67.7 |
| Recovery, % | 98.1 | 97.7 | 98.4 | 98.6 | 97.5 | 98.0 | 98.2 | 79.2 | 84.6 |
| Washing with water | Yes | Yes | Yes | Yes | Yes | No | No | Yes | Yes |

Note:
[1]A: Centrifugal;
[2]B: Falling film;
[3]C: Pot

We claim:
1. In a process for producing sucrose fatty acid polyester by microemulsion or solvent-free transesterification of sucrose, the improvement which comprises the steps of (a) heating a molten mixture of sucrose, at least 4 moles per mole of sucrose of a fatty acid lower alkyl ester, a basic transesterification catalyst, a fatty acid alkali metal soap and/or a sucrose fatty acid ester at a temperature from 120° C. to 180° C. under a vacuum less than 10 mmHg with stirring at a linear speed of 1.0 to 50 m/second, (b) acidifying the reaction product with an acid to a pH below 6, (c) subjecting the acidified reaction product to molecular distillation, and (d) recovering the sucrose fatty acid polyester from the residue in a purified form.

2. A process according to claim 1 wherein the fatty acid lower alkyl ester is the $C_1$-$C_4$ alkyl ester of a $C_6$-$C_{22}$ fatty acid.

3. A process according to claim 1 wherein the basic transesterification catalyst is the hydroxide, carbonate or lower alkoxide of an alkali metal.

4. A process according to claim 1 wherein at least 8 moles of the fatty acid lower alkyl ester are used per mole of sucrose.

5. A process according to claim 3 wherein 1 to 10% by weight of the fatty acid lower alkyl ester of the basic transesterification catalyst is used.

6. A process according to claim 5 wherein 3 to 8% by weight of the fatty acid lower alkyl ester of the basic transesterification catalyst is used.

7. A process according to claim 1 wherein the fatty acid alkali metal soap is the sodium, potassium or lithium salt of a $C_6$-$C_{22}$ fatty acid.

8. A process according to claim 7 wherein 3 to 15% of the soap is used relative to the total weights of sucrose and the fatty acid lower alkyl ester.

9. A process according to claim 8 wherein 5 to 10% of the soap is used relative to the total weights of sucrose and the fatty acid lower alkyl ester.

10. A process according to claim 1 wherein 3 to 30% of the sucrose fatty acid ester is used relative to the total weights of sucrose and the fatty acid lower alkyl ester.

11. A process according to claim 10 wherein 5 to 15 of the sucrose fatty acid ester is used relative to the total weights of sucrose and the fatty acid lower alkyl ester.

12. A process according to claim 1 wherein the molecular distillation is performed under a vacuum from $10^{-1}$ to $10^{-3}$ mmHg.

13. A process according to claim 1 wherein the molecular distillation is performed at a temperature from 60° C. to 150° C.

14. A prcoess according to claim 13 wherein the molecular distillation is performed at a temperature from 80° C. to 120° C.

15. A process according to claim 1 wherein the molecular distillation is performed at a film thickness of $10^{-1}$ to $10^{-2}$ mm.

16. A process according to claim 1 wherein the pH is below 5.

17. A process according to claim 1 further including the step of washing the residue with water after the molecular distillation.

18. A process according to claim 1 wherein the fatty acid lower alkyl ester is the $C_1$-$C_4$ alkyl ester of a $C_6$-$C_{22}$ fatty acid; wherein the basic transesterification catalyst is the hydroxide, carbonate or lower alkoxide of an alkali metal; wherein at least 8 moles of the fatty acid lower alkyl ester are used per mole of sucrose; wherein 1 to 10% by weight of the fatty acid lower alkyl ester of the basic transesterification catalyst is used; wherein the fatty acid alkali metal soap is the sodium, potassium or lithium salt of a $C_6$-$C_{22}$ fatty acid; wherein 3 to 15% of the soap is used relative to the total weights of sucrose and the fatty acid lower alkyl ester, wherein 3 to 30% of the sucrose fatty acid ester is used relative to the total weights of sucrose and the fatty acid lower alkyl ester; wherein the molecular distillation is performed under a vacuum less than 1 mmHg, at a temperature from 60° C. to 150° C. and at a film thickness of less than 1 mm; and wherein the reaction product is acidified to a pH below 5.

19. A process according to claim 18 wherein 3 to 8% by weight of the fatty acid lower alkyl ester of the basic transesterification catalyst is used; wherein 5 to 10% of the soap is used relative to the total weights of sucrose and the fatty acid lower alkyl ester; wherein 5 to 15% of the sucrose fatty acid ester is used relative to the total weights of sucrose and the fatty acid lower alkyl ester; wherein the molecular distillation is performed under a vacuum from $10^{-1}$ to $10^{-3}$ mmHg, at a temperature from 80° C. to 120° C.; and at a film thickness of $10^{-1}$ to $10^{-2}$ mm.

* * * * *